United States Patent [19]

Findlay et al.

[11] Patent Number: 5,514,550

[45] Date of Patent: May 7, 1996

[54] NUCLEIC ACID TEST ARTICLE AND ITS USE TO DETECT A PREDETERMINED NUCLEIC ACID

[75] Inventors: John B. Findlay; Janice M. Mayer, both of Rochester; Marlene M. King, Penfield; Fred T. Oakes, Rochester, all of N.Y.; Chu-an Chang, El Cerrito; Corey H. Levenson, Oakland, both of Calif.

[73] Assignee: Johnson & Johnson Clinical Diagnostics, Inc., Rochester, N.Y.

[21] Appl. No.: 300,297

[22] Filed: Sep. 2, 1994

Related U.S. Application Data

[63] Continuation of Ser. No. 971,880, Nov. 4, 1992, abandoned, which is a continuation of Ser. No. 571,560, Sep. 4, 1990, abandoned, which is a continuation-in-part of Ser. No. 306,954, Feb. 3, 1989, abandoned.

[51] Int. Cl.$^6$ .................... C12Q 1/68; C12P 19/34
[52] U.S. Cl. .................... 435/6; 435/91.2; 536/24.32
[58] Field of Search .................. 435/6, 91.2; 536/24.32; 935/77, 78

[56] References Cited

U.S. PATENT DOCUMENTS

| | | | |
|---|---|---|---|
| 4,358,535 | 5/1986 | Falkow et al. | 435/5 |
| 4,563,419 | 1/1986 | Ranki et al. | 435/6 |
| 4,673,657 | 6/1987 | Christian | 436/501 |
| 4,683,195 | 7/1987 | Mullis et al. | 435/6 |
| 4,683,202 | 7/1987 | Millis | 435/91 |
| 4,727,019 | 2/1988 | Valkirs et al. | 435/5 |
| 4,965,188 | 10/1990 | Mullis et al. | 435/6 |
| 4,988,617 | 1/1991 | Landegren et al. | 435/6 |

FOREIGN PATENT DOCUMENTS

| | | |
|---|---|---|
| 200381 | 11/1986 | European Pat. Off. . |
| 237362 | 9/1987 | European Pat. Off. . |
| 235726 | 9/1987 | European Pat. Off. . |
| 281927 | 9/1988 | European Pat. Off. . |
| 85-05451 | 12/1985 | WIPO . |
| 88-01302 | 2/1988 | WIPO . |
| 8801302 | 2/1988 | WIPO . |

OTHER PUBLICATIONS

Matthews et al, Analytical Biochemistry, vol. 169, p. 1–25, Feb. 1988.

*Primary Examiner*—Mindy Fleisher
*Assistant Examiner*—James Ketter

[57] ABSTRACT

A nucleic acid test article can be used to detect a targeted nucleic acid found in a specimen. The test article includes a substrate having two opposing surfaces and a water-insoluble nucleic acid probe attached in a distinct zone of one of the surfaces. The probe is prepared from a water-insoluble particle to which is covalently attached an oligonucleotide which is complementary to the targeted nucleic acid. Substantially none of the probe is embedded within the surface of the substrate. Particularly useful test articles have a multiplicity of water-insoluble probes located in distinct zones on one of the substrate surfaces. These probes are useful for the detection of a multiplicity of targeted nucleic acids, particularly after amplification by polymerase chain reaction.

14 Claims, 1 Drawing Sheet

NUCLEIC ACID TEST ARTICLE AND ITS USE TO DETECT A PREDETERMINED NUCLEIC ACID

REFERENCE TO RELATED APPLICATIONS

This application is a continuation of U.S. Ser. No. 07/971,880 filed Nov. 4, 1992, now abandoned, which in turn is a continuation of U.S. Ser. No. 07/571,560, filed Sep. 4, 1990, now abandoned, which in turn is a continuation-in-part of U.S. Ser. No. 306,954 filed Feb. 3, 1989, by John. B. Findlay et al. now abandoned.

FIELD OF THE INVENTION

This invention relates to diagnostic procedures, and particularly diagnostic procedures for the detection of nucleic acids. It also relates to a test article useful in such procedures.

BACKGROUND OF THE INVENTION

Nucleic acid hybridization is a well known procedure for investigating the identity of nucleic acids. Hybridization is based on complementary base pairing. When single-stranded nucleic acids are incubated in solution, complementary base sequences pair to form double-stranded hybrid molecules. These molecules can be separated when desired by denaturation.

Also known are nucleic acid probe assays which can be used to assay a specimen for the presence of a predetermined (also known as a target) nucleic acid for diagnosis of disease, genetic defects, genetic engineering or characterization, or for testing blood, food or other materials for contamination or other medical or research purposes [see, for example, U.S. Pat. No. 4,358,535 (issued Nov. 9, 1982 to Falkow et al), WO-A-88/01302 (published Feb. 25, 1988) and references mentioned therein].

Among nucleic acid probe assays are what are known in the art as "sandwich" assays in which two probes are used to sandwich the nucleic acid of interest therebetween in a three-part hybridized product. Generally, one probe is a "capture" probe which is immobilized or capable of becoming so on a solid surface, and the other probe is detectably labeled or capable of becoming so. Sandwich assays have the advantage that the predetermined nucleic acid need not be immobilized directly to a solid support, and offer the potential for higher specificity because two hybridization reactions are required for detection instead of one.

Most "capture" probes used in probe assays are generally composed of a sequence of nucleotides which form an oligonucleotide which is complementary to at least one nucleic acid sequence of the predetermined nucleic acid being detected. Various methods are known for attaching oligonucleotides to solid supports for affinity chromatography separation of nucleic acids and for probe assays. Among the considerable literature describing such methods are WO-A-88/01302 (noted above), EP-A-0 235 726 (published Sep. 9, 1987) and U.S. Pat. No. 4,673,657 (issued Jun. 16, 1987 to Christian).

A significant advance in the art is described in U.S. Pat. No. 4,683,195 (issued Jul. 28, 1987 to Mullis et al) and U.S. Pat. No. 4,683,202 (issued Jul. 28, 1987 to Mullis). Without going into extensive detail, these patents describe an amplification process wherein primers are hybridized to nucleic acid templates in the presence of a polymerization agent (such as a polymerase) and four deoxyribonucleoside triphosphates, and extension products are formed from the primers. These products are denatured and used as templates in a cycling reaction which amplifies the number and amount of predetermined nucleic acid to facilitate its subsequent detection. This amplification process can be carried out cyclically as many times as desired to produce a larger quantity of detectable material from a small amount of predetermined nucleic acid.

Once the target sequence has been adequately amplified to detectable quantities, the mode of detection is not critical. Many techniques for detection are described in the art including the use of probes labeled with radioisotopes, biotin or enzymes (linked to the probe through a biotin-avidin linkage) or gel electrophoresis. Other probes are used for capturing the amplified product on a support.

U.S. Pat. No. 4,727,019 (Feb. 23, 1988 to Valkirs et al) describes analytical methods and apparatus in which nucleic acids can be detected using probes immobilized directly to a porous substrate (such as a membrane) in a localized region. Alternatively, the probe can be embedded within the porous matrix. While directly attaching probes to such substrates or embedding them therein may provide accurate and sensitive assays where the predetermined nucleic acid is present in the test specimen in generally large concentrations, it has limitations where the concentrations are very low. As research proceeds in this field of art, the need to detect lower quantities (even a single molecule) is of greater importance. Thus, many conventional methods and apparatus for nucleic acid testing are deficient.

Similarly, an analytical method is described in EP-A-0 200 381 (published Nov. 5, 1986) which utilizes nucleic acids attached to polymeric particles which are embedded within a porous matrix. Moreover, several probes can be embedded in distinct regions of the matrix so that a multiplicity of nucleic acids can be detected simultaneously.

The desire to detect one or more nucleic acids simultaneously remains in the art. However, as noted above, there is also a need to detect increasingly lower concentrations of those acids. This requires high sensitivity by the probes and analytical procedures.

SUMMARY OF THE INVENTION

The problems noted above are overcome with a nucleic acid test article comprising a substrate having at least first and second opposing surfaces, and having affixed in at least one distinct zone of at least one of the opposing surfaces, a water-insoluble nucleic acid probe, the probe comprising an oligonucleotide complementary to a predetermined nucleic acid, which oligonucleotide is covalently attached to a water-insoluble particle, and substantially none of the probe being embedded within the opposing surface.

Moreover, a method for the detection of a predetermined nucleic acid comprises:

A. contacting a specimen suspected of containing a predetermined nucleic acid with the nucleic acid test article described above, to form a hybridized product of predetermined nucleic acid and the water-insoluble probe, B. prior to, simultaneously with or subsequently to step A, contacting the specimen with a detectably labeled probe which is complementary to the predetermined nucleic acid to form an immobilized sandwich product of the predetermined nucleic acid hybridized with both the water-insoluble probe and labeled probe, C. separating the immobilized sandwich product from nonimmobilized materials, and D. detecting the immobilized sandwich product as an indication of the amount of predetermined nucleic acid in the specimen.

More particularly, a method for the detection of a predetermined nucleic acid comprises:

A. amplifying a predetermined nucleic acid found in a specimen in the presence of complementary primers, deoxyribonucleotide triphosphates and a polymerization agent, B. contacting the amplified predetermined nucleic acid with the nucleic acid test article described above, to form an immobilized hybridized product of predetermined nucleic acid and the water-insoluble probe, C. separating the immobilized product from nonimmobilized materials, and D. detecting the immobilized product as an indication of the amount of predetermined nucleic acid in the specimen.

The present invention provides a means for achieving rapid and accurate detection of one or more nucleic acids in a specimen, such as a biological specimen. It is particularly advantageous that the present invention allows highly sensitive assays where the targeted nucleic acid is present in extremely low concentrations. Moreover, the test article of this invention is easily prepared and has considerable manufacturing efficacies. Because the probes are composed of water-insoluble particles, they are easily deposited on a suitable substrate or incorporated into test devices for use later on. Thus, the use of probe solutions and accompanying disadvantages are avoided.

The advantages are achieved by using water-insoluble probes which are affixed to substrates in a specific location thereon. Moreover, the probes are not embedded within the substrate, as taught in the art, so that more surface area of the probe is exposed to the test specimen, and assay sensitivity is enhanced. An important advantage of this invention is that a multiplicity of predetermined nucleic acids can be detected simultaneously using a multiplicity of water-insoluble probes affixed to the substrate in individual locations. In a preferred embodiment, the test article of this invention is incorporated within a self-contained test device which may contain all reagents for the assay. If some reagents are not preincorporated, the test device can be a container for the assay after reagent addition.

DETAILED DESCRIPTION OF THE INVENTION

Figure 1:
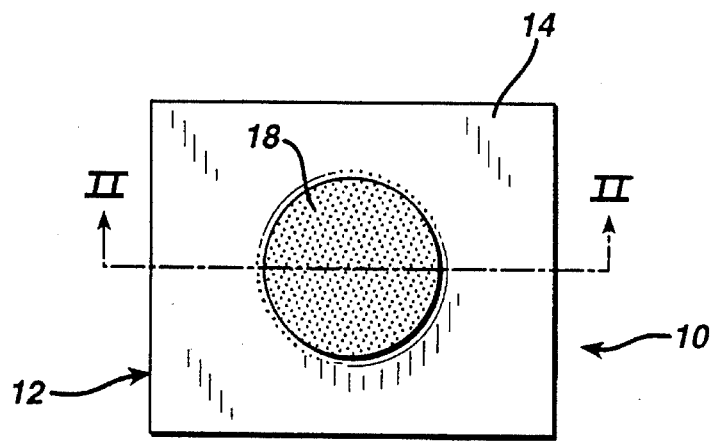
FIG. 1 is a top view of a test article of this invention having a water-insoluble probe immobilized in a localized area of the substrate.

As used herein in referring to primers, probes or oligomer fragments to be detected or used in detection of a nucleic acid, the term "oligonucleotide" refers to a molecule comprised of two or more deoxyribonucleotides or ribonucleotides, and preferably more than three. The exact size is not critical but depends upon many factors including the ultimate use or function of the oligonucleotide. The oligonucleotide may be derived synthetically or by cloning.

The term "primer" refers to an oligonucleotide, whether naturally occurring or synthetically produced, which is capable of acting as a point of initiation of synthesis when subjected to conditions in which synthesis of a primer extension product complementary to a nucleic acid strand is induced. Such conditions include the presence of nucleotides (such as the four standard deoxyribonucleotide triphosphates) and an agent for polymerization such as a DNA polymerase, and suitable temperature and pH.

In one embodiment, the primer contains a double-stranded, labeled nucleic acid region adjacent to a single-stranded region. The single-stranded region contains a nucleic acid sequence which is sufficiently complementary to the template strand to hybridize therewith. The double-stranded region, or tail, of the primer can be labeled with a detectable moiety which is capable of producing a detectable signal or which is useful in capturing or immobilizing the extension product.

In other and preferred embodiments, the primer is entirely single-stranded. Preferably, the primer is a single-stranded oligodeoxyribonucleotide. It must be sufficiently long to prime the synthesis of extension products in the presence of the polymerization agent, but its exact size will vary depending upon the use contemplated, the complexity of the target sequence, reaction temperature and the source of the primer. Generally, each primer used in this invention will have from about 15 to about 50 nucleotides, and preferably, it has from about 20 to about 30 nucleotides.

The primers used in the present invention are selected to be "substantially" complementary to the different strands of each specific sequence to be amplified. This means that they must be sufficiently complementary to hybridize with their respective strands to form the desired hybridized products. Noncomplementary bases may be incorporated therein as long as they do not interfere with hybridization and formation of extension products. Preferably, the primers have exact complementarity to obtain the best results in amplification efficiency.

Primers useful herein can be obtained from a number of sources or prepared using known techniques and equipment, including for example, an ABI DNA Synthesizer (available from Applied Biosystems) or a SAM-I Synthesizer (available from Biosearch, Inc.) and known methods for their use. Naturally occurring primers isolated from biological sources are also useful (such as restriction endonuclease digests).

As used herein the term "probe" refers to an oligonucleotide, naturally occurring or synthetically produced, which is not used as a primer, but which is designed to be substantially complementary to one or more sequences of a nucleic acid so as to form a hybridized product. Further, a probe is generally designed for either "capture" or "detection" of the resulting hybridized product. Capture probes are those which are either attached to an insoluble material in some fashion or are capable of becoming attached at some time in the assay, such as by absorption or complexation through specific binding ligands (for example, avidin-biotin complexes). Detection probes either have a detectable label incorporated therein, or have a moiety which is capable of reacting with a detectable moiety, for example through an avidin-biotin complex. Other embodiments of capture and detection probes are known in the art.

The present invention is directed to the detection of one or more predetermined nucleic acids present in the same or different test specimens. Such specimens can include cellular or vital material, hair, body fluids or other materials containing genetic, vital or bacterial DNA or RNA which can be detected. While the primary purpose of such detection would be diagnostic in nature, the invention could also be used to improve the efficiency of cloning DNA or messenger RNA, for tissue typing, or for obtaining large amounts of a desired nucleic acid from a mixture of nucleic acids resulting from chemical synthesis.

The present invention is advantageously carried out using a test article having a substrate to which is affixed in a suitable manner one or more capture probes. Each probe is water-insoluble because it is composed of a water-insoluble particle of some type having one or more molecules of an oligonucleotide covalently affixed thereto. This oligonucleotide is complementary to the nucleic acid of interest to a sufficient degree that they will form hybridized products in the course of the assay.

This test article is now discussed in more detail, but it is to be understood that further embodiments would be readily apparent to one skilled in the art.

The article substrate can be any porous or nonporous surface to which the probe can be readily affixed and which will allow ready access of solution containing the predetermined nucleic acid to the probe. There must be some type of bonding between probe and substrate in order to keep the probe in place during manufacturing and storage, and in some cases, during an assay. It is important, however, to the sensitivity desired in using the test article, whether the substrate is porous or nonporous, that the probe be predominantly on the outer surface (or surfaces) of the substrate. This means that the probe is not embedded to a significant degree into the substrate. It is to be understood that-in the course of manufacture of the article using porous substrates that some of the probe may become buried or embedded therein, but in the present invention, it is expected that less than 20 percent of the probe is so situated. In preferred embodiments, the substrate is a nonporous material, and the one or more probes are completely on one or more of its outer surfaces.

The substrate is more clearly defined as having a configuration (described below) which has at least two opposing outer surfaces. Such surfaces are generally parallel, but need not be completely parallel (for example the inside and outside surfaces of a curved bottom of a test tube). Generally, the substrate is a flat sheet, membrane or film having nominal thickness and outer surfaces for retaining probe. A detailed description of one embodiment of a test article is provided in copending U.S. Ser. No. 339,923 (filed Apr. 17, 1989 by Schnipelsky et al).

Substrate materials useful herein include, but are not limited to, cellulosic materials, metals, polymers, ceramics, glasses or fabrics configured into any useful form including films, membranes, foils, papers (such as photographic or thermal print papers including raw stock papers that have not been treated, finished, sized or coated in any manner, or papers which have been treated, finished, sized or coated, for example with polymeric latices), cuvettes, test tubes, test slides or strips. Particularly useful substrates include polymeric films, polymeric or cellulosic microporous membranes, such as those manufactured by Pall Corp. (for example, Biodyne™ or Loprodyne™ membranes), or polymeric latex-coated, or uncoated cellulosic papers. Most useful substrates are papers which are substantially nonporous and uncoated, such as thermal print papers.

Figure 2:
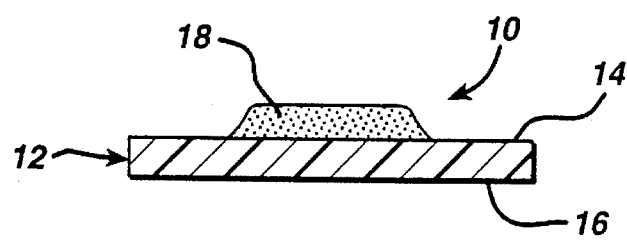
FIG. 2 is a cross-sectional view taken along line II—II of FIG. 1.

Several embodiments of test articles are illustrated in the attached drawings. Looking at FIGS. 1 and 2, test article 10 is shown as a simple piece of polymeric film substrate 12 having upper and lower opposing surfaces 14 and 16. Water-insoluble nucleic acid probe 18 is immobilized in a deposit in the center of opposing surface 14 of substrate 12.

Figure 3:
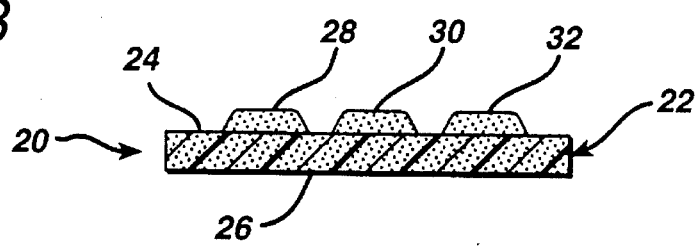
FIG. 3 is a cross-sectional view similar to FIG. 2 of a different test article embodiment of this invention, having a multiplicity of localized probes on a substrate.

Another embodiment of a test article is shown in the cross-sectional view of FIG. 3. Test article 20 comprises porous substrate 22 having opposing upper and lower surfaces 24 and 26. Located in distinct regions of opposing surface 24 are water-insoluble probe deposits 28, 30 and 32, which can contain the same or different probes.

Figure 4:
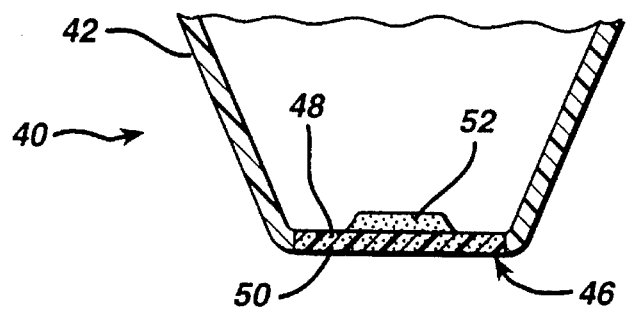
FIG. 4 is a cross-sectional view of still another embodiment of this invention in which a water-insoluble probe is localized on a membrane located at the bottom of a test well.

Still another embodiment is a test well of a disposable test device (described below) shown in cross-section in FIG. 4. Test well 40 has conical wall 42 and a porous membrane 46 at the bottom thereof. Membrane 46 has opposing upper and lower surfaces 48 and 50, and on opposing surface 48 is a water-insoluble probe deposit 52.

The probes can be affixed to the substrates using any suitable technique. Generally, the probe is deposited in a suitable manner and dried to form a coated region of probe on the substrate, and affixation is by physical means. Alternatively, the affixing can be provided through chemical reaction if desired using reactive groups on either or both substrate and probe, or reactive linking groups. Preferably, the probe is merely dried down in one or more distinct areas of the substrate (such as dots, stripes or other patterns, each distinct area generally having a surface area of from about 1 to about 30 mm$^2$). In some instances, the probes may be resuspended when contacted with fluids used in an assay.

The probes themselves are prepared using water-insoluble particles of regular or irregular shape. If spherical, they generally have an average diameter of from about 0.1 to about 10 µm. Preferably, the particles are spherical and have an average diameter of less than about 5 µmeters. The particles can be prepared from any suitable material to which oligonucleotides can be covalently attached, including, but not limited to, glasses, ceramics, metals, magnetizable materials, polymeric materials, sols, gels and other materials readily apparent to one skilled in the art.

Preferably, the particles are prepared from polymers having active groups for covalent oligonucleotide attachment. Useful active groups include carboxy, amino, sulfhydryl, aldehyde, activated 2-substituted ethylsulfonyl, vinylsulfonyl, active halogen atoms, nitroaryl and others readily apparent to one skilled in the art. Particularly useful particles are polymeric particles derived from one or more ethylenically unsaturated polymerizable monomers having one or more of the following reactive groups: carboxy, activated 2-substituted ethylsulfonyl, vinylsulfonyl or active halogens. Further details about such particles, including useful monomers, methods of preparing them and attachment of oligonucleotides, are known in the art (for example, in EP-A-0 302 715, published Feb. 8, 1989).

Attachment of oligonucleotides to particles can be accomplished using standard procedures which will depend upon the type of particles (that is, the reactive groups) and what reactive group of the oligonucleotide is used (for example, reactive groups on the pyrimidine or purine base moieties, or part of a terminal nucleotide, either 5' or 3'). Various procedures are described, for example, in WO-A-88/01302 (noted above).

The coverage of oligonucleotide on the particles may be important in some assays for improved sensitivity. Generally, it is desired to attach as many molecules of the oligonucleotide on the particles as possible. Because the particles have a high surface area to volume ratio as compared to other substrates, the high density is advantageous. Preferably, the coverage is generally from about 100 to about 3000 pmoles of oligonucleotide per mg of particles.

As noted above, the water-insoluble probe is affixed in a distinct area of one or more surfaces of the substrate. Each area can be the same or different in size and shape. In a preferred embodiment where there are a multiplicity of distinct areas having the same or different probe, the areas are kept apart sufficiently that each area can be detected separately. In this embodiment, the various probes can be used for detecting different predetermined nucleic acids from the same or different specimens, or they can be used to detect the same nucleic acid but act as controls.

The present invention also encompasses a method for using the test article described herein to detect a predetermined nucleic acid. The general description of the method is provided above. In one embodiment, the test article is used in a sandwich hybridization assay where a second probe is used to provide detection of the resulting three-part hybrid. This second probe is also complementary to the predetermined nucleic acid, and contains a moiety which provides detection in some manner (as discussed above). Preferably, the second probe is labeled with avidin, biotin, antibody, antigen, hapten, lectin, sugar (or another specific binding moiety), or other detectable moieties described below. Most preferably, the label is an enzyme, which when contacted with appropriate substrates or dye-forming reagents, will provide a detectable dye on the test article.

Procedures for attaching labels and preparing probes are well known in the art, for example, as described by Agrawal et al, *Nucleic Acid Res.*, 14, pp. 6227–45 (1986). Useful labels include radioisotopes, electron-dense reagents, chromogens, fluorogens, phosphorescent moieties, dyed particles, ferritin and other magnetic particles, chemiluminescent moieties and enzymes. Useful enzymes include, glucose oxidase, peroxidase, uricass, alkaline phosphatase and others known in the art. Substrates and dye forming compositions for such enzymes are well known.

In a particularly preferred embodiment, the label is peroxidase, and at some point in the assay, hydrogen peroxide and suitable dye-forming compositions are added to provide a detectable dye. For example, useful dye-providing reagents include tetramethylbenzidine and derivatives thereof, and leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide. A particularly useful dye-providing compositions is described in the examples below.

Detection of the presence of the probe which is in the resulting hybridized product can be achieved using suitable and known detection equipment and procedures. Certain probes may be visible to the eye without the use of detection equipment. It is also useful for the method to be carried out in a suitable container (described below).

It is preferred that prior to hybridization of the predetermined nucleic acid with the probes as described above, the predetermined nucleic acid be amplified to increase the number of molecules vailable for detection.

Amplification, as described in more detail in U.S. Pat. No. 4,683,202 (noted above), involves a chain reaction for producing, in exponential quantities relative to the number of reaction steps involved, at least one predetermined nucleic acid. The product will be a discrete nucleic acid duplex with termini corresponding to the ends of the specific primers employed. Any source of nucleic acid, purified or not, can be utilized as the starting material provided it contains or is suspected of containing the nucleic acid targeted for detection. A mixture of nucleic acids can be employed if desired. The predetermined nucleic acid can be a fragment or the entire acid. Moreover, more than one nucleic acid can be amplified simultaneously by using a specific set of primers and probes for each acid to be amplified.

The present invention is useful for detection of a nucleic acid having two complementary strands. Most nucleic acids of interest already are double-stranded, such as those found in DNA. However, single-stranded nucleic acids, such as mRNA, can be similarly detected after it is converted to a double-stranded sequence using reverse transcriptase.

A specific nucleic acid to be reproduced is used as a template. If the acid contains two strands, it is necessary to separate the strands (called denaturation), either as a separate step or simultaneously with the formation of primer extension products. Denaturation can be accomplished using any suitable physical, chemical or enzymatic means as described in the art. Heating to a suitable temperature is a preferred means.

Once the separated strands are available for use, synthesis of additional nucleic acid strands can be carried out using two or more primers (at least one of which is labeled as described above) in a buffered aqueous solution at a pH of from about 7 to about 9. Preferably, a molar excess of the two primers is added to the buffered solution, and specific amounts are taught in the art. The deoxyribonucleoside triphosphates dATP, dCTP, dGTP and dTTP are also added to the synthetic mixture in adequate amounts and the resulting solution is heated to about 90°–100° C. for up to 10 minutes, and preferably from about 1 to about 4 minutes. After this heating, the solution is preferably cooled to room temperature, and an appropriate agent for inducing (or catalyzing) the formation of primer extension products is introduced. This inducing agent is generally known in the art as a polymerization agent. Reaction to form these products is carried out under known conditions (generally from room temperature to that temperature at which polymerization no longer occurs).

In one embodiment, the primers used are unlabeled, and detection of amplified product is achieved using one or more radio-labeled deoxyribonucleotide tri-phosphates to form extension products.

The polymerization agent may be any reagent, or combination of reagents, which will function to accomplish the synthesis of primer extension products, including enzymes (for example, *E. coli* DNA polymerase I, T4 DNA polymerase, Klenow polymerase, reverse transcriptase and others known in the art). Particularly useful enzymes are thermally stable enzymes, cloned or naturally occurring, such as those obtained from various Thermus bacterial species. Other polymerization agents are described in U.S. Pat. No. 4,683,202 (noted above).

Preferred thermal-stable enzymes are DNA polymerases isolated from from Thermus aquaticus or produced from a genome thereof, such as those described in EP-A-0 258 017 (published Mar. 2, 1988). Other useful enzymes are described by Rossi et al, *Syst. Appl. Microbiol.* 7(2–3), pp. 337–341, 1986. Many useful polymerases are commercially available. Generally, the synthesis of extension products will be initiated at the 3' end of each primer and proceed in the 5' to 3' direction along the template until synthesis is terminated. Some polymerization agents (for example, reverse transcriptase) may proceed in the 3' to 5' direction alone the template.

The newly formed primer extension products comprising the newly synthesized strands and their respective primers form double-stranded molecules with the initial target strands which are used in the succeeding steps of the method. These strands are then separated by denaturation to provide single-stranded molecules, onto which new nucleic acids are synthesized as described above. Additional reagents may be needed to keep the amplification procedure going, after which most of the extension products will consist of the predetermined nucleic acid hybridized to the two primers (that is, as complementary products).

The steps of strand separation and extension product synthesis can be repeated as often as needed to produce the desired quantity of the predetermined nucleic acid needed for detection. Generally, the sequence of steps is repeated at least once, and preferably at least 10 to 30 times.

At any point in the method of this invention after the generation of at least one primer extension product, that product can be hybridized with a probe, either a capture probe or a detectably labeled probe as described herein. This contact of probes and extension product can occur simultaneously or sequentially with other hybridization reactions in the assay.

It is also useful for the amplification method to be carried out in a suitable container. The most crude container would be a test tube, flask or beaker, but more sophisticated containers have been fashioned in order to facilitate automated procedures. For example, a cuvette constructed to provide certain temperature characteristics during the practice of the method is described in U.S. Ser. No. 273,781 (filed Nov. 21, 1987 by Burdick et al). A particularly useful container for performing the method and which incorporates the test article of this invention is described in U.S. Ser. No. 339,923 (noted above). Other useful containers could be suitably fashioned for automated or manual use of the method of this invention.

In order for the complementary product to be detected, it is important for the water-insoluble product to be separated from the nonimmobilized materials in the reaction medium. This can done by filtration, washing, centrifugation or other suitable separation techniques.

Particularly useful separation means are microporous filter membranes such as the polyamide membranes marketed by Pall Corp. (for example as Loprodyne™ or Biodyne™ membranes). They can be used uncoated or precoated with surfactants or other materials which facilitate the analytical procedures. In one embodiment, the membrane is incorporated into the cuvette wherein the detection method occurs. Generally, such membranes have average pore sizes such that substantially all of the probe remains on the surface thereof. Preferably, the pore size is from about 1 to about 10 μmeter.

The membranes can be used as a separate substrate with suitable containers for carrying out other steps of the assay. Preferably, however, it is mounted as part of a disposable test device. Various test devices are known in the art including those described in U.S. Pat. No. 3,825,410 (issued Jul. 23, 1974 to Bagshawe), U.S. Pat. No. 3,888,629 (issued Jun. 10, 1975 to Bagshawe), U.S. Pat. No. 3,970,429 (issued Jul. 20, 1976 to Updike) and U.S. Pat. No. 4,446,232 (issued May 1, 1984 to Liotta). Particularly useful devices are described in U.S. Ser. No. 98,248 (filed Sept. 18, 1987 by Hinckley et al) and in U.S. Ser. No. 339,923 (noted above). Useful disposable test devices containing microporous membranes are marketed by Eastman Kodak Company as Surecell™ test devices.

The method described herein can be used to provide the detection or characterization of predetermined nucleic acids associated with infectious diseases, genetic disorders or cellular disorders such as cancers. It may also be used in forensic investigations and DNA tissue typing. For purposes of this invention, genetic diseases include specific deletions or mutations in genomic DNA from any organism, such as sickle cell anemia, cystic fibrosis, α-thalassemia, β-thalessemia and others readily apparent to one skilled in the art. Various infectious diseases can be diagnosed by the presence in a clinical sample of small quantities of specific DNA sequences characteristic of the organism, whether it be a yeast, bacterium or virus. Such bacteria which can be detected include, but are not limited to, Streptococcus, Salmonella, Chlamydia, Gonorrhea, Shigella and Listeria. Viruses which are detectable include, but are not limited to, herpes, rubella, human papilloma virus, cytomegalovirus, Epstein barr virus, hepatitis and retroviruses such as HTLV-I and HIV-I. The detection of β-globin DNA for the determination of sickle cell anemia can also be accomplished with this invention. Protozoan parasites, yeasts and molds are also detectable. Other detectable species would be readily apparent to one skilled in the art. The invention is particularly useful for the detection of the presence of retroviruses, such as HIV-I, in test samples. In such assays, a probe is used having an oligonucleotide complementary to a nucleic acid sequence of HIV-I DNA, for example a sequence in the gag region.

The following examples are provided to illustrate, but not limit, the practice of the present invention. All percentages are by weight unless otherwise noted.

Examples 1 and 2 illustrate assays for HIV-I DNA using what is termed a "flow through" procedure whereby a water-insoluble probe is immobilized on a filter membrane in a disposable test device. Hybridization with the HIV-I DNA target nucleic acid occurs to form a water-insoluble product, followed by washing water-soluble materials through the filter membrane. The water-insoluble product remaining on the membrane is detected on its surface.

Example 3 illustrates as assay for HIV-I DNA and β-globin DNA using what is termed a "flow by" procedure whereby two water-insoluble probes are immobilized on a solid substrate having substantially no porosity. Hybridization of the probes with the HIV-I DNA and β-globin DNA target nucleic acids occurs to form water-insoluble products. Water-soluble materials are washed away over the substrate and the remaining water-insoluble hybrid products are then detected on the substrate surface.

EXAMPLE 1

Preparation of Nucleic Acid Test Article and Its Use in Detection of HIV-I DNA Fragment Materials:

A leuco dye solution was prepared containing 2-(4-hydroxy-3,5-dimethoxyphenyl)-4,5-bis(4-methoxyphenyl)imidazole as follows:

Solid leuco dye (to make a 0.1% solution) was dissolved in a solution of 20 weight % poly(vinylpyrrolidone) in sodium phosphate buffer (5 mmolar). This solution was then added to a solution containing hydrogen peroxide (10 mmolar), 4'-hydroxyacetanilide electron transfer agent (5 mmolar) and diethylenetriaminepentaacetic acid chelating agent (10 μmolar) in sodium phosphate buffer to produce a final concentration of 1% poly(vinylpyrrolidone) and 0.005% leuco dye.

Succinylated casein was prepared by reacting casein with an equal weight of succinic anhydride for four hours at 25° C., then purifying the product by dialysis.

The predetermined DNA fragment detected in the example was a 180 nucleotide segment of the gag region (core protein) of the HIV-I genome cloned into a derivative of M13 vector and prepared using standard procedures.

The primers used in the amplification of the predetermined DNA strands had the following nucleotide sequences using the standard abbreviations for adenine (A), guanine (G), thymine (T) and cytosine (C):

5'-X-TTTGGTCCTTGTCTTATGTCCAGAATGC-3' and
5'-ATAATCCACCTATCCCAGTAGGAGAAAT-3' wherein X represents a biotintetraethylene glycol molecule, prepared and attached by procedures described in WO-A-89/02931, incorporated herein by reference.

DNA polymerase was isolated from *Thermus aquaticus* according to the procedures described in EP-A-0 258 017 (1 unit corresponds to 10 mmoles of dNTP incorporated into the primer extension product in 30 minutes at 37° C.).

A streptavidin-horseradish peroxidase conjugate was obtained from Zymed Labs (San Francisco), and was diluted 1:8000 with a phosphate buffered saline solution containing casein (0.5%), 3-(N-morpholino)-propanesulfonic acid buffer (100 mmolar, pH 7.5) and preservative (0.01%). The final conjugate concentration was 156 ng/ml. The phosphate buffered saline solution contained sodium phosphate (25 mmolar, pH 7.3) and sodium chloride (75 mmolar).

Preparation of Probe:

A water-insoluble probe used in the example was prepared in the following manner.

Polymeric particles (2 μmeters) comprised from poly(styrene-co-acrylic acid)(97.5:2.5 molar ratio) using standard latex polymerization procedures, then stored as a suspension (0.45% solids) in glycine buffer (0.1 molar, pH 8.5).

An oligonucleotide complementary to the predetermined HIV-I DNA target sequence was used to prepare the probe. It had the following sequence:

5'-X-ATCCTGGGATTAAATAAAATAGTAAGAATGT-3' wherein X represents an amino group attached to the probe through a polyethyleneglycol spacer, as described in WO 89/02932, incorporated herein by reference.

The suspension of polymeric particles was washed twice with 2-(N-morpholino)ethanesulfonic acid buffer (0.1 molar, pH 6). A sample of particles (30 g) in 2-(N-morpholino)ethanesulfonic acid buffer (1 ml) was mixed with 1-(3-dimethylaminopropyl)-3-ethylcarbodiimide hydrochloride (0.15 ml of 100 mg/ml in the same buffer) and the oligonucleotide (0.0288 ml of 57.3 OD/ml nanopure water, 1.65 OD units). The resulting mixture was rotated end-over-end at 20°–25° C. for 15 hours, centrifuged, and the particles were washed three times with nanopure water and resuspended therein (0.45% solids).

Three different concentrations of the resulting water-insoluble probe were prepared:

Probe A: 334 picomoles probe/mg particles,
Probe B: 835 picomoles probe/mg particles, and
Probe C: 1670 picomoles probe/mg particles.

The water-insoluble probe described above (1 μl of 0.45% suspension) was deposited in a defined region (less than about 2 mm$^2$) of each of several microporous membranes (Biodyne™ A nylon membranes coated with 1 g/m$^2$ succinylated casein) located in test wells of Surecell™ disposable test devices (Eastman Kodak Co.). The probe suspension was allowed to dry for about 30 minutes at room temperature. The resulting test articles were then used in the assay described below.

Assay Procedure:

To a buffer solution containing tris(hydroxymethyl)aminomethane buffer (10 mmolar, pH 8), potassium chloride (50 mmolar), magnesium chloride (10 mmolar) and gelatin (10 μg) were added the primers described above (100 pmoles of each), dNTPs (1.5 mmolar of each), the polymerase described above (7.5 units) and human placenta DNA (Sigma, 1 μg). In addition, the DNA target ($10^{-16}$ molar) described above was added, and the total volume was 100 μl.

A control (100 μl) was prepared containing human placenta DNA (10 μg/ml) containing the β-globin gene as target, and the appropriate primers, specific for β-globin DNA which are known in the art, one primer being biotinylated.

Each solution described above was placed into a polypropylene microcentrifuge tube, primer extension products were formed, and amplification promoted using 30 consecutive thermal cycles as follows:

| | |
|---|---|
| 70° C. rising to 95° C. | 1 minute |
| 95° C. | 0.5 minute (denature) |
| 95° C. lowering to 55° C. | 1.25 minutes |
| 55° C. | 0.5 minute (hybridize) |
| 55° C. rising to 70° C. | 0.75 minute |
| 70° C. | 1 minute (extend) |

After amplification through the 30 thermal cycles, 5 μl aliquots of each mixture were added to a solution (95 μl) containing tris(hydroxymethyl)aminomethane buffer (10 mmolar, pH 8), potassium chloride (50 molar), magnesium chloride (10 mmolar) and gelatin (1 μg/10 ml solution), heat denatured (5 minutes at 95° C.), then added to the test wells of the Surecell™ test devices described above (about 95 μl of each solution in each well).

Tape was placed over each well to seal them, and the devices were incubated at 42° C. for 5 minutes to hybridize the amplified HIV-I DNA fragment to the water-insoluble probe immobilized in the test wells. The tape was then removed off each test well, followed by washing with a buffered solution (250 μl) containing phosphate buffer (10 mmolar, pH 7.4), sodium chloride (150 mmolar), ethylenediaminetetraacetic acid (1 mmolar) and sodium decyl sulfate (1%) at 55° C.

The peroxidase conjugate described above (50 μl, 7.8 ng) was added to each test well, and the devices were incubated at room temperature for 2 minutes. A second wash (250 μl) was carried out using the buffered solution noted above. The leuco dye solution (100 μl) was added to each test well followed by another incubation at room temperature for 2 minutes. The resulting dye-forming reaction was stopped by the addition of sodium azide (100 μl of 0.1%), and the resulting dye was observed on the membranes.

The results were graded visually on a scale of 0 to 5, with zero being no density and 5 being the highest density. The results in the following table are the average of two separate readings for each probe concentration.

No signal was observed in the test devices to which the control solution was added. Background values were obtained from density readings on the membrane areas where there was an absence of

TABLE

| Probe Test | Dye Density | |
|---|---|---|
| | Test Sample | Background |
| Probe A | 3.65 | 0.25 |
| Probe B | 3.5 | 0 |
| Probe C | 3.35 | 0 |

EXAMPLES 2

HIV-I DNA Detection

This example demonstrates the detection of HIV-I DNA using a microporous filtration membrane as the substrate on which probes are immobilized.

Materials and Methods:

Polymeric particles comprising poly[styrene-co-m & p-(2-chloroethylsulfonylmethyl)styrene] (95.5:4.5 molar ratio, 2.2 μm average size) were prepared by the methods described in U.S. Ser. No. 081,206 (filed Aug. 3, 1987 by Sutton et al), incorporated herein by reference.

Casein was attached to these particles in the following manner: A solution of casein (Sigma Chemical, 4.94 ml of 2.57 mg/ml in 0.05 molar borate buffer, pH 8.5), thimerosal (0.01%) and the noted suspension of polymeric particles (17.7 ml in borate buffer, 0.0637 g/ml) was rotated end-over-end for 16 hours at room temperature. The mixture was then centrifuged and the buffer solution was discarded. The resulting pellet was resuspended in glycine buffer (0.1 molar, 50 ml, pH 8.5) and thimerosal (0.01%). This mixture was centrifuged, and the resulting pellet was resuspended in glycine buffer (250 ml) to 0.45% solids.

A sample of the particle suspension (50 ml) containing 2.54 g of particles was washed three times with borate buffer (10 ml, 0.05 molar, pH 8.5), mixed with succinic anhydride (Sigma Chemical, 0.762 ml) in a solution of dimethyl sulfoxide (10 mg/ml) and allowed to react for four hours at room temperature. The mixture was centrifuged and the solution discarded. The resulting pellet was washed three time with glycine buffer (50 ml, 0.01 molar, pH 8.5), and resuspended in glycine buffer to 0.45% solids.

A suspension of the particles (15 ml, 0.0045 g/ml) in glycine buffer was centrifuged, and the pellet resuspended in 2-(N-morpholino)ethanesulfonic acid buffer (0.1 molar, pH 6). This procedure was repreated twice and the resulting pellet was mixed with 1-(3-dimethylaminopropyl)-3-ethyl-carbodiimide hydrochloride (0.338 ml of a solution of 100 mg/ml in the same buffer) and the oligonucleotide (0.654 μl of a solution of 5.73 OD/ml of buffer) having the sequence noted below. This suspension was rotated end-over-end for sixteen hours at room temperature and centrifuged, and the pellet was resuspended in nanopure water (15 ml). This centrifuging procedure was repeated three times, and the resulting pellet was suspended in water to provide a 0.45% solid suspension of water-insoluble probe.

The oligonucleotide had the sequence (using standard abbreviations for the bases):

5'-ATCCTGGGATTAAATAAAATAGTAAGAATGT-3'

Assay:

The assay for HIV-I DNA was carried out according to the procedure described in Example 1. The water-insoluble probes was deposited in a defined region of a microporous membrane and allowed to dry as noted in that Example.

The amount of dye formed on the membrane in the assay was visually graded on a scale of from 0 to 5 (zero being no density and 5 being the highest density). The background value was obtained from a density reading on the membrane area where no water-insoluble probe was present. The dye density reading for the assay was determined to be about 4.8 while the background density was about 0.5.

EXAMPLE 3

Determination of HIV-I DNA and β-Globin DNA

This example demonstrates as assay for HIV-I DNA and β-globin DNA using a substantially nonporous, uncoated paper as the substrate on which two water-insoluble probes are immobilized.

Materials:

Eppendorf tubes and a heater were obtained from Eppendorf Corporation.

Ektamate™ thermal print paper (noncoated) was obtained from Eastman Kodak Company and used as the substantially nonporous, uncoated paper substrate.

The HIV-I primers were the same as those described in Example 1 above.

The β-globin DNA primers had the following sequences:

5'-X-ACACAACTGTGTTCACTAGC-3' and 5'-CAACTTCATC-CACGTTCACC-3' wherein X is a biotin molecule prepared and attached as described above in Example 1 for the HIV-I primers.

The β-globin DNA probe had the following sequence:

5'-X-CTCAAACAGACACCATGGTGCACCTGACTC-3' wherein X is the same as described for the HIV-I DNA probe.

The probes and primers were prepared using standard phosphoramidite chemistry, purified by high pressure liquid chromatography and characterized by standard sequencing procedures.

A water-insoluble probe for HIV-I DNA was prepared as described in Example 1 above using particles composed of poly(styrene-co-acrylic acid)(95:5 molar ratio, 2 μm). The probe (2 μl of a 0.45% suspension) was deposited on a defined region (2 mm diameter spot) of Ektamate™ thermal print paper (about 19×8 mm in size), and allowed to dry at room temperature. The β-globin probe DNA was similarly prepared and deposited in a separate region (2 mm-diameter) of the same paper substrate.

The paper substrate was then affixed to one side of a plastic material (a laminate of a polyester with either polyethylene or polypropylene). The other side of the plastic material was sealed with heat onto the first side to form an enclosed pouch. This pouch contained an inlet pipette tip for injecting fluids into the pouch for eventual contact with the probe therein, and an outlet means to allow fluids to exit the pouch. Fluid reagents were then forced into the pouch to be in contact the probe before exiting the pouch.

A reaction mixture (100 μl total volume) for polymerase chain reaction comprised:

tris(hydroxymethyl)aminomethane buffer (10 mmolar, pH 8.3), potassium chloride (50 mmolar), magnesium chloride (10 mmolar), dNTPs (1.5 mmolar of each), primers (1 μmolar), gelatin (0.01%), and DNA polymerase isolated from Thermus aquaticus (7.5 units).

The HIV-I DNA target nucleic acid was M13/HIV (a 180 base pair segment of HIV-I cloned into M13 DNA phage) or HUT cell line DNA (a cell line that contains a single integrated copy of the HIV-I genome). The β-globin target nucleic acid was human placental DNA which is assumed to contain two copies of the β-globin gene per cell.

Assay:

A solution of both HIV-I and β-globin targets (10 μl, about $10^{-16}$ molar each) and the polymerase chain reaction mixture (100 μl) were added to Eppendorf tubes in an Eppendorf heating unit and subjected to polymerase chain reaction for 30–33 cycles using the protocol: incubation at 95° C. for 30 seconds (denaturation), incubation at 55° C. for 30 seconds (hybridization) and incubation at 70° C. for 1 minute (polymerization).

A portion (10 μl) of the solution containing amplified target nucleic acids was then diluted with a buffer solution (130 μl) comprising tris(hydroxymethyl)aminomethane buffer (10 mmolar, pH 8.3), potassium chloride (50 mmolar), magnesium chloride (10 mmolar) and gelatin (0.01%). The resulting solution was then heated in an Eppendorf tube at 95° C. for 5 minutes to denature the double stranded target nucleic acids. The heated solution was transferred to a pipette and injected into the pouch described above in a manner to insure even coverage of the thermal paper surface having the immobilized probes. The pouch was then incubated at 42° C. for 5 minutes to anneal the corresponding probes to the respective single stranded HIV-I and β-globin nucleic acid targets. The fluid was removed from the pouch by either forcing the liquid out with air pressure or drawing off the fluid using a syringe.

A wash solution was injected into the pouch twice. This solution comprised: 250 μl of a buffer solution comprising sodium dihydrogen phosphate (10 mmolar, pH 7.4), sodium chloride (150 molar) and ethylenediaminetetraacetic acid (1 mmolar), and decyl sulfate (1%), and had been preheated to 55° C. The fluid was removed after the second wash, and the streptavidin-horseradish peroxidase conjugate of Example 1 (200 μl) was then injected into the pouch which was then incubated at room temperature for two minutes. The fluid was then removed and the leuco dye solution noted above (200 μl) was injected into the pouch followed by another incubation at room temperature for 1–2 minutes. Finally, the fluid was removed. A solution of sodium azide (200 μl of 0.1% solution) was injected into the pouch to stop the reaction and the dye present on the thermal paper was visually graded on a scale from 0 to 5 with 5 representing the highest dye density. Background readings were taken from regions of the paper having no immobilized probe. The dye density reading for the HIV-I DNA and β-globin DNA targets were 3.8 and 4.2, respectively, while the background reading was 0.5.

The invention has been described in detail with particular reference to preferred embodiments thereof, but it will be understood that variations and modifications can be effected within the spirit and scope of the invention.

We claim:

1. A method for the detection of one or more predetermined nucleic acids, said method comprising:

A. amplifying one or more predetermined nucleic acids found in a specimen in the presence of complementary primers, deoxyribonucleotide triphosphates and a polymerization agent, at least one of said primers being detectably labeled, to provide one or more detectably labeled, amplified predetermined nucleic acids, B. contacting said one or more detectably labeled, amplified predetermined nucleic acids with a nucleic acid test article comprising a substrate selected from the group consisting of a nonporous coated paper, a nonporous polymeric film, and a nonporous, noncoated paper, and having affixed in each of at least two distinct areas on said substrate, a water-insoluble nucleic acid probe, said nucleic acid test article being disposed in a self-contained test device, each of said probes comprising an oligonucleotide complementary to a nucleic acid sequence of said one or more detectably labeled, amplified predetermined nucleic acids, which oligonucleotides are covalently attached to polymeric particles which are affixed predominantly on the outer surface of said substrate, to form an immobilized hybridized product of each of said one or more detectably labeled, amplified predetermined nucleic acids and said water-insoluble probe in each of said distinct areas of said substrate, C. washing said substrate to separate nonimmobilized materials from each immobilized product, and D. detecting each immobilized product in each of said distinct areas of said substrate as a detection of the amount of one or more predetermined nucleic acids in said specimen, wherein step C is carried out within about 4 minutes.

2. The method of claim 1 wherein said substrate is a nonporous, noncoated paper.

3. The method of claim 1 wherein said polymeric particle has a diameter of from about 0.1 to about 5 μmeters.

4. The method of claim 1 wherein said oligonucleotide is covalently attached to a particle prepared from polymers having active carboxy, amino, sulfhydryl, aldehyde, activated 2-substituted ethylsulfonyl, vinylsulfonyl, halogen atoms or nitroaryl groups.

5. The method of claim 1 wherein said primer is biotinylated and detection of said immobilized product is carried out using a conjugate of streptavidin and an enzyme.

6. The method of claim 5 wherein said enzyme is glucose oxidase, peroxidase, uricase or alkaline phosphatase, and detection is carried out by contacting said immobilized product with a substrate and a dye-forming composition for said enzyme.

7. The method of claim 6 wherein said enzyme is peroxidase, and said substrate is hydrogen peroxide which is reacted with a triarylimidazole leuco dye.

8. The method of claim 1 wherein each distinct area on said substrate has a surface area of from about 1 to about 30 $mm^2$.

9. The method of claim 1 wherein said substrate is a nonporous, coated paper.

10. The method of claim 1 wherein said substrate is a nonporous polymeric film.

11. The method of claim 1 wherein step B is carried out within about 10 minutes.

12. A method for the detection of one or more nucleic acid sequences of HIV-I DNA, said method comprising:

A. amplifying one or more nucleic acid sequences of HIV-I DNA found in a biological specimen in the presence of complementary primers, deoxyribonucleotide triphosphates and a polymerase isolated from a Thermus bacterial species, at least one of said primers being detectably labeled, to provide one or more detectably labeled, amplified nucleic acid sequences of HIV-I DNA, B. contacting said one or more detectably labeled, amplified nucleic acid sequences of HIV-I DNA with a nucleic acid test article comprising a substrate selected from the group consisting of a nonporous coated paper, a nonporous polymeric film, and a nonporous, noncoated paper, having affixed in each of at least two distinct areas on said substrate, a water-insoluble nucleic acid probe, said nucleic acid test article being disposed in a self-contained test device, each of said probes comprising an oligonucleotide complementary to said one or more detectably labeled, amplified nucleic acid sequences of HIV-I DNA, which oligonucleotides are covalently attached to polymeric particles having an average diameter of from about 0.1 to about 5 μmeters which are affixed predominantly on the outer surface of said substrate, to form an immobilized hybridized product of each of one or more of said detectably labeled, amplified nucleic acid sequences of HIV-I DNA and said water-insoluble probe in each of said distinct areas of said substrate, C. washing said substrate to separate nonimmobilized materials from each immobilized product, and D. detecting each immobilized product in each of said distinct areas of said substrate as a detection of one or more nucleic acid sequences of HIV-I DNA in said specimen, wherein step C is carried out within about 4 minutes.

13. The method of claim 12 wherein at least one primer is biotinylated, and detection of said immobilized product is accomplished by contacting it with a conjugate of streptavidin and an enzyme.

14. The method of claim 13 wherein said conjugate comprises peroxidase, and contact of said conjugate and product is followed by contact of the product with a leuco dye composition which provides a dye in the presence of hydrogen peroxide and peroxidase.

* * * * *